United States Patent [19]

Boelens et al.

[11] 4,057,515

[45] Nov. 8, 1977

[54] PERFUME COMPOSITIONS

[75] Inventors: Harmannus Boelens, Huizen; Jan Theodor Marie François Maessen, Naarden; Leendert Maarten van der Linde, Huizen, all of Netherlands

[73] Assignee: N.V. Chemische Fabriek "Naarden", Naarden, Netherlands

[21] Appl. No.: 569,317

[22] Filed: Apr. 17, 1975

Related U.S. Application Data

[63] Continuation of Ser. No. 8,729, Feb. 4, 1970, abandoned.

[30] Foreign Application Priority Data

Feb. 4, 1969 Netherlands ........................ 6901750

[51] Int. Cl.[2] ........................ A61K 7/46; C07C 45/00

[52] U.S. Cl. ................................ 252/522; 252/89 R; 260/598; 424/69

[58] Field of Search ............................ 260/488 B, 598; 252/522

[56] References Cited

U.S. PATENT DOCUMENTS 3,574,715 4/1971 Marbet ................................ 424/488

FOREIGN PATENT DOCUMENTS 295,084 4/1965 Netherlands ........................ 252/522

*Primary Examiner*—Albert T. Meyers
*Assistant Examiner*—A. P. Fagelson
*Attorney, Agent, or Firm*—Stevens, Davis, Miller & Mosher

[57] ABSTRACT

Perfume compositions are provided which are based upon certain cycloalkylidenebutanals. The perfume compositions comprising the subject cycloalkylidenebutanals.

3 Claims, No Drawings

PERFUME COMPOSITIONS

This is a continuation of application Ser. No. 8729, filed Feb. 4, 1970 now abandoned.

This invention relates to new perfume compositions and compounds which are suitable for use as an active ingredient in perfume compositions.

It has long been recognized in the art that various organic compounds are suitable for use as the active ingredient in perfumes.

An object of this invention is therefore to provide new perfume compositions.

A further object of this invention is to provide novel compounds which can impart a pleasing scent and accordingly can be used in perfume compositions.

The objects of this invention are accomplished by the discovery of certain novel cycloalkylidenebutanals of the following general formula:

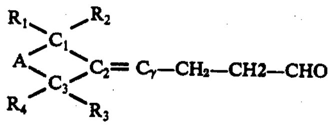
(I)

wherein

A together with the carbon atoms $C_1$, $C_2$ and $C_3$ forms a monocyclic or polycyclic aliphatic radical, each of $R_1$, $R_2$, $R_3$ and $R_4$ is independently hydrogen or an alkyl radical of from 1 to 5 carbon atoms, and when A represents ethylene or propylene at least one of $R_1$, $R_2$, $R_3$ and $R_4$ is an alkyl radical of from 1 to 5 carbon atoms.

According to a preferred embodiment of the invention, the total number of carbon atoms represented in formula (I) is from 11 to 28.

According to a still more preferred embodiment of the invention, the total number of carbon atoms represented in formula (I) is from 11 to 18 carbon atoms.

The compounds of the formula (I) have been discovered to possess a strong odor which makes them particularly suited for use in perfume compositions. These compounds may be mixed with other components commonly found in perfumes, such as aromatic components, in order to obtain specific, characteristically widely divergent perfume compositions, imparting in general a fruity-green scent with a distinct scent of a very floral muguet. The compounds of the present invention may be used therefore in compositions such as cosmetics, soaps, soap powders, detergents, toilet waters, lotions, aerosols, creams, powders and any other composition to which the distinctive odor of the compounds is desired.

It is quite unexpected that the compounds of the present invention were found to possess the desirable properties of the muguet scent. Thus, although it is known that a few $\gamma$, $\delta$ unsaturated carbonyl compounds can be used as perfumes, it was unexpectedly discovered that cyclic aldehydes of Formula (I) possess the desirable muguet odor.

The compounds of Formula (I) may be prepared in several ways.

As a first method of synthesizing the subject compounds of Formula (I), spirohydropyrans are heated over a copper catalyst at a temperature ranging between 200° C and 400° C. This conversion may be carried out continously.

The starting material spirohydropyrans may be represented by the following formula:

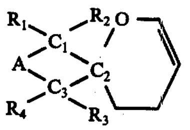
(II)

wherein

A, $R_1$, $R_2$, $R_3$, and $R_4$ have the previously assigned meanings.

As a second method of synthesizing the compounds of Formula (I), vinylcyclanoles and a vinyl ether are heated in the presence of a catalytic amount of acid at a temperature ranging from 50° C to 150° C. A variation of this method has been described in Dutch Patent Application No. 295,084, as well as in Bull. Soc. Chim. de France, 1964, pages 2618–2635.

The vinylcyclanoles used to produce the compounds of Formula (I) have the following formula:

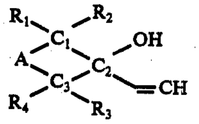
(III)

wherein

A, $R_1$, $R_2$, $R_3$ and $R_4$ have the previously assigned meanings.

The vinyl ether has the following structure $H_2C{=}CH{-}OR$ (IV)

The R group is not critical to the nature of the products of the invention as it is split off during the reaction. It may be, for examle, a lower alkyl group. Thus, a typical vinyl ether of Formula (IV) is vinylethyl ether.

The following examples are illustrative of the preparation of compounds within the scope of the invention.

EXAMPLE I

Preparation of 4-(tricyclodecylidene)-butanal-1 (First Method)

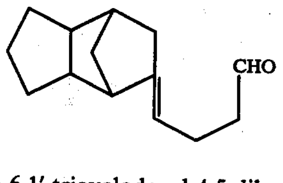

100 g of spiro-6,1'-tricyclodecyl-4,5-dihydropyran

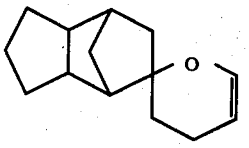

is passed through a glass reactor tube filled with 100 g of bronze powder (B.D.H. quality) mixed with 10 g of hyflo (filtering aid of Johns-Manville Sales Corp., New York, U.S.A.) for five hours at a temperature of 300° to 320° C. The reaction product is condensated in a cooler connected to the reactor and consists of:

a. about 20% of first run components, b. about 35% of unconverted spiro-6,1'-tricyclodecyl 4,5-hydropyran, c. about 20% of isomeric tricyclodecyl-dihydropyrans, d. about 25% of 4-(tricyclodecylidene)-butanal-1.

The fractions (b) and (c) may be returned to the reactor. 4-(tricyclodecylidene)-butanal-1 is isolated from the reaction mixture by fractional distillation. There is thus obtained 20 g of 4-(tricyclodecylidene)-butanal-1 with a boiling point of 105° to 110° C at 3 mm Hg; n 20/D: 1.5099.

The product consists of 2 isomers, both cis and trans, which may be separated via preparative gas chromatography.

One component has a green floral, muguet-like odor; NMR spectrum:

δ = 4.89 (*t*, broad, J = 6-7, 1, > C = $C\underline{H}$-$CH_2$—)

δ = 9.70 (*t*, J = 1.5, 1, —$CH_2$ — $C\underline{H}O$;

A second component has a fruity-green floral, strong muguet-like odor;

NMR spectrum:

δ = 5.13 (*t*, broad, J = 6-7, 1, > C = $C\underline{H}$ — $CH_2$—)

δ = 9.68 (*t*, *J* = 1.5, 1, —$CH_2$—$C\underline{H}O$)

EXAMPLE II

Preparation of 4-(tricyclodecylidene)-butanal-1 (Second Method)

In a 1-liter reaction flask, equipped with thermometer and reflux condenser, are introduced:

180 g of 5-vinyl 5-hydroxyhexahydro 4,7-methanolindane

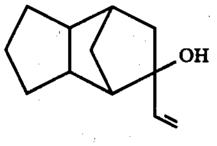

200 g of xylene 95 g of vinylethyl ether and 0.025 g of p-toluene sulphonic acid.

The reaction mixture is heated to the boiling point and during the reaction the temperature is raised from 60° C to 120° C in five hours. During this reaction period another 114 g of vinylethyl ether is added. After cooling to 20° C 3 g of triethylamine is added and the reaction mixture poured out into water. The organic layer is washed until neutral with water and distilled under reduced pressure.

There is thus obtained:

50 g of first runnings, boiling point at 1 mm Hg: 58°-99° C, n 20/D: 1.5010;

10 g of intermediate fraction, boiling point at 1 mm Hg: 99°-103° C; n 20/D: 1.4980;

100 g of 4-(tricyclodecylidene)-butanal-1, boiling point at 1 mm Hg

103°-105° C; n 20/D: 1.5100. 50 g of residue.

According to G.L.C., NMR and I.R. analysis, the product was fully identical to the product mentioned under Example I and consisted of two isomers (cis/trans).

EXAMPLE III 4-(tricyclodecenylidene)-butanal-1

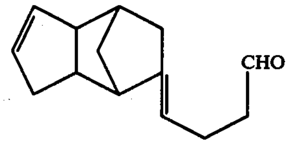

The procedure of Example II was repeated to produce the above compound in a yield of 60%. The product was found to have a boiling point at 1 mm Hg: 111°-114° C; n 20/D: 1.5179.

Component (a): green floral, muguet-like odor: NMR spectrum:

δ = 4.90 (t, broad, J = 6-7, 1, > C = $C\underline{H}$ — $CH_2$—)

δ = 5.55 (*m*, 2, —$C\underline{H}$ = $C\underline{H}$—)

δ = 9.72 (*t*, J = 1.5, 1, —$CH_2$ — $C\underline{H}O$)

Component (b): green floral, strong muguet-like odor; NMR spectrum:

δ = 5.15 (*t*, broad, J = 6-7, 1, > C = $C\underline{H}$ — $CH_2$-)

δ = 5.55 (*m*, 2, —$C\underline{H}$ = $C\underline{H}$—)

δ = 9.72 (*t*, *J* = 1.5, 1, —$CH_2$ — $C\underline{H}O$) CL EXAMPLE IV 4-(cyclododecylidene)-butanal-1

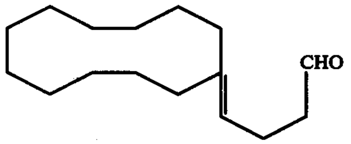

Following the same procedure set forth in Example II, the subject compound was produced in a yield of 50%. The product has a green-woody, faint floral odor.

The compound was found to have a boiling point at 1 mm Hg: 142°-146° C; n 20/D: 1.4974.

NMR spectrum:

δ = 5.11 (*t*, broad, J = 6-7, 1, > C = $C\underline{H}$ — $CH_2$—)

δ = 9.70 (*t*, J = 1.5, 1, —$CH_2C\underline{H}O$)

EXAMPLE V 4-(decalinylidene-2')-butanal-1

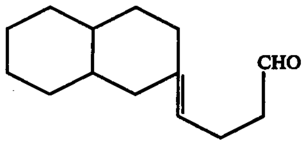

The subject compound was produced by following the procedure set forth in Example II to produce a product having two components in a yield of 45%.

The compound was found to have a boiling point at 1 mm Hg: 99-101° C; n 20/D: 1.4988.

Component (a): woody-floral, hydroxycitronellal-like, NMR spectrum:

δ = 5.00 (t, broad, J = 6-7, 1, > C = $C\underline{H}CH_2$-)

δ = 9.70 (t, J = 1.4, 1, —$CH_2C\underline{H}O$)

Component (b): woody-floral, hydroxycitronellal-like, NMR spectrum:

δ = 5.00 (t, broad, *J* = 6-7, 1, > C = $C\underline{H}$ — $CH_2$—)

δ = 9.69 (t, J = 1.4, 1, —$CH_2C\underline{H}O$)

Having described the preparation of representative compounds within the scope of the invention, the following illustrative examples are presented to show actual compositions prepared according to the claimed invention.

EXAMPLE VI

EXAMPLE VI

| Lilas composition | |
|---|---|
| 50 g | of cinnamie alcohol |
| 40 g | of heliotropin |
| 300 g | of phenylethanol |
| 10 g | of laurylaldehyde, 10% in diethylphthalate |
| 5 g | of 4-(tricyclodecylidene)-butanal-1 |
| 20 g | of methyl-alpha-nonylenate |
| 20 g | of iso-eugenol |
| 40 g | of anisaldehyde |
| 75 g | of alpha-amylcinnamicaldehyde |
| 100 g | of benzyl acetate |
| 40 g | of indole, 10% in diethylphthalate |
| 300 g | of terpineol |
| 1.000 g | |

EXAMPLE VII

EXAMPLE VII

| Phantasy perfume | |
|---|---|
| 20 g | of styrax resinoid |
| 20 g | of dimethylcarbinyl acetate |
| 80 g | of benzyl acetate |
| 15 g | of oil of lemon Messina |
| 5 g | of laurylaldehyde, 10% in diethylphthalate |
| 15 g | of methylnonylacetaldehyde 10% in diethylphthalate |
| 10 g | of 4-(decalinylidene-2') butanal-1 |
| 10 g | of 2-heptyltetrahydrofuran |
| 25 g | of amyl salicylate |
| 50 g | of ylang-ylang oil |
| 50 g | of geranium oil Bourbon |
| 150 g | of alpha-ionone |
| 50 g | of benzyl salicylate |
| 20 g | of indole, 10% in diethylphthalate |
| 150 g | of hydroxycitronellal |
| 150 g | of linalool |
| 150 g | of linalyl acetate |
| 30 g | of phenylethyl acetate |
| 1.000 g | |

EXAMPLE VIII

EXAMPLE VIII

| Soap perfume | |
|---|---|
| 10 g | of dimethylbenzylcarbinyl acetate |
| 10 g | of iso-camphylcyclohexanol |
| 30 g | of coumarin |
| 5 g | of 1,1,3,4,4,6-hexamethyl 7-acetyltetralin |
| 100 g | of benzyl acetate |
| 10 g | of 4-(tricyclodecenylidene)butanal-1 |
| 10 g | of oil of thyme |
| 100 g | of Lavandin oil |
| 150 g | of 4-tert butylcyclohexyl acetate |
| 150 g | of terpineol |
| 50 g | of citronellol |
| 50 g | of geraniol |
| 140 g | of phenylethanol |
| 80 g | of alpha-amyl cinnamic aldehyde |
| 10 g | of 2.4-dimethyl 6-butyl 2.6-dihydropyran |
| 5 g | of undecylene aldehyde |
| 40 g | of amyl salicylate |
| 50 g | of hydroxycitronellal |
| 1.000 g | |

EXAMPLE IX

EXAMPLE IX

| Phantasy perfume | |
|---|---|
| 5 g | of heliotropin |
| 60 g | of cinnamic alcohol |
| 40 g | of benzyl acetate |
| 20 g | of methyl alpha-nonylenate |
| 5 g | of ylang-ylang oil |
| 15 g | of 4-(cyclododecylidene) butanal-1 |
| 5 g | of metnhyljonon |
| 10 g | of benzyl salicylate |
| 20 g | of nerolidol |
| 60 g | of linalool |
| 50 g | of alpha-hexyl cinnamic aldehyde |
| 180 g | of nerol |
| 260 g | of citronellol |
| 270 g | of hydroxycitronellal |
| 1.000 g | |

What is claimed is:

1. A perfume composition comprising conventional perfume constituents and an effective amount of 4-(tricyclodecylidene)-butanal-1 to impart a fruity-green, muguet-like note.

2. A perfume composition comprising conventional perfume constituents and an effective amount of 4-(tricyclodecenylidene)-butanal-1 to impart a fruity-green, muguet-like note.

3. A perfume composition conprising conventional perfume constitutents and an effective amount of 4-(decalinylidene-2' )-butanal-1 to impart a fruity-green, muguet-like note.

* * * * *